(12) United States Patent
Nordman et al.

(10) Patent No.: US 6,596,140 B2
(45) Date of Patent: Jul. 22, 2003

(54) MULTI-CHANNEL CAPILLARY ELECTROPHORESIS DEVICE AND METHOD

(75) Inventors: Eric S. Nordman, Palo Alto, CA (US); Richard T. Reel, Hayward, CA (US)

(73) Assignee: Applera Corporation, Foster City, CA (US)

( * ) Notice: Subject to any disclaimer, the term of this patent is extended or adjusted under 35 U.S.C. 154(b) by 1 day.

(21) Appl. No.: 09/846,855

(22) Filed: May 1, 2001

(65) Prior Publication Data

US 2002/0162745 A1 Nov. 7, 2002

(51) Int. Cl.[7] .................. G01N 27/447; G01N 27/453; G01N 30/02
(52) U.S. Cl. .................. 204/452; 204/461; 204/603; 204/612
(58) Field of Search ................. 204/456, 461, 204/452, 606, 601, 603, 612; 422/70

(56) References Cited

U.S. PATENT DOCUMENTS

| 4,592,089 A | * | 5/1986 | Hartman ............... 348/135 |
| 4,832,815 A | | 5/1989 | Kambara et al. |
| 5,192,412 A | | 3/1993 | Kambara et al. |
| 5,268,080 A | | 12/1993 | Kambara et al. |
| 5,277,780 A | | 1/1994 | Kambara |
| 5,314,602 A | | 5/1994 | Kambara et al. |
| 5,356,776 A | * | 10/1994 | Kambara et al. ........... 204/461 |

(List continued on next page.)

FOREIGN PATENT DOCUMENTS

| EP | 0 882 982 | 12/1998 |
| WO | 98/09161 | 3/1998 |
| WO | 98/49549 | 11/1998 |
| WO | 99/24828 | 5/1999 |
| WO | 00/73780 | 12/2000 |

OTHER PUBLICATIONS

Dolnik et al., "Capillary electrophoresis on microchip," *Electrophoresis*, 2000, 21, 41–54.
Garcia Campana et al., "Miniaturization of Capillary Electrophoresis Systems Using Micromachining Techniques, "*J. Microcolumn Separations*, 10(4), 339–355, (1998).
Huang et al., "End–Column Detection for Capillary Zone Electrophoresis," *Anal. Chem.*, 63(2) 189–192, Jan. 15, 1991.
Krishnamoorthy et al., "Analysis of Sample Injection and Brand–Broadening in Capillary Electrophoresis Microchips," Techinal Proceedings of the MSM 2000, San Diego, CA, March 27–29, 2000.
Robson et al., "Capillary Electrochromatography: A Review," 357–372, 1997.
Swinney et al., "Detection in capillary electrophoresis," *Electrophoresis*, 2000, 21, 1239–1250.
Takahashi et al., "Multiple Sheath–Flow Gel Capillary–Array Electrophresis for Multicolor Fluorescent DNA Detection," *Anal. Chem.*, 1994, 66, 1021–1026.
Taylor et al., "Axial–beam absorbance detection for capillary electrophoresis," *Journal of Chromatography*, 550(1991) pp. 831–837.

(List continued on next page.)

*Primary Examiner*—Nam Nguyen
*Assistant Examiner*—Alex Noguerola
(74) *Attorney, Agent, or Firm*—Harness, Dickey & Pierce, P.L.C.

(57) ABSTRACT

Embodiments of a device and method are described which provide for control over the distortion of a sample zone upon exiting an electrophoresis separation channel. According to the teachings herein (i) the downstream regions of the channels, near the outlet ends, and/or (ii) the detection chamber, is/are configured so that distortion of one or more sample zones passing from the channels into and across the detection chamber can be controlled (e.g., reduced) in a fashion affording enhanced detectability. In certain embodiments, the lumens along the end regions of the separation channels progressively expand.

38 Claims, 5 Drawing Sheets

U.S. PATENT DOCUMENTS

| | | |
|---|---|---|
| 5,366,608 A | 11/1994 | Kambara |
| 5,439,578 A | 8/1995 | Dovichi et al. |
| 5,529,679 A | 6/1996 | Takahashi et al. |
| 5,667,656 A | 9/1997 | Kambara |
| 5,741,412 A | 4/1998 | Dovichi et al. |
| 5,754,524 A * | 5/1998 | Wark .......................... 204/461 |
| 5,790,727 A | 8/1998 | Dhadwal et al. |
| 5,833,826 A | 11/1998 | Nordman |
| 5,858,187 A | 1/1999 | Ramsey et al. |
| 6,017,434 A | 1/2000 | Simpson et al. |
| 6,045,676 A | 4/2000 | Mathies et al. |
| 6,156,177 A * | 12/2000 | Takahashi et al. .......... 204/452 |
| 6,159,353 A | 12/2000 | West et al. |
| 6,174,675 B1 | 1/2001 | Chow et al. |

OTHER PUBLICATIONS

Woolley et al., "Capillary Electrophoresis Chips with Integrated Electrochemical Detection," *Anal. Chem.*, 70(4), pp. 684–688, Feb. 15, 1998.

Woolley et al., "Ultra–high–speed DNA fragment separations using microfabricated capillary array electrophoresis chips," *Proc. Natl. Acad. Sci USA*, vol. 91, pp. 11348–11352, November 1994.

XI et al., "Axial–Beam On–Column Absorption Detection for Open Tubular Capillary Liquid Chromatography," *Anal. Chem.*, vol. 62, no. 15, pp. 1580–1585, Aug. 1, 1990.

* cited by examiner

MULTI-CHANNEL CAPILLARY ELECTROPHORESIS DEVICE AND METHOD

FIELD OF THE INVENTION

The present invention relates to electrophoretic separation systems for the analysis of bio-molecules, such as nucleic acids. More particularly, this invention relates to a multi-channel capillary electrophoresis device and method wherein the distortion of a sample zone exiting from the end of a channel is controlled thereby resulting in enhanced detectability of such sample zone.

REFERENCES

Dovichi et al., U.S. Pat. No. 5,439,578 (1995).
Grossman and Colburn, Capillary Electrophoresis Theory and Practice, Chapter 1, Academic Press (1992).
Grossman, U.S. Pat. No. 5,374,527 (1994).
Holman, Heat Transfer, Fourth Edition, McGraw-Hill (1976).
Kambara et al., U.S. Pat. No. 5,192,142 (1993).
Madabhushi et al., U.S. Pat. No. 5,552,028 (1996).
Sambrook et al., eds., Molecular Cloning: A Laboratory Manual, Second Edition, Chapter 5, Cold Spring Harbor Laboratory Press (1989).
Takahashi et al., U.S. Pat. No. 5,529,679 (1996).
Woolley, et al., Ultra-high-speed DNA fragment separations using microfabricated capillary array electrophoresis chips, Proc. Natl. Acad. Sci., vol. 91, pp. 11348–11352, Nov. 1994, Biophysics.

BACKGROUND OF THE INVENTION

Electrophoretic separations of bio-molecules are critically important in modern biology and biotechnology, comprising an important component of such techniques as DNA sequencing, protein molecular weight determination, genetic mapping, and the like. A particularly preferred electrophoresis format is capillary electrophoresis (CE), where the electrophoresis is performed in a channel, such as a capillary tube or a groove in a microfabricated chip, wafer or plate, having a small internal diameter. Capillary electrophoresis results in enhanced separation performance over traditional slab-based formats because the superior ability of the narrow-bore capillary to tolerate resistive heating allows for high electrical fields to be employed thereby resulting in fast separations in which sample diffusion is minimized.

In traditional CE systems, detection of a sample subsequent to separation is performed during electrophoresis while the sample is still located inside the channel (referred to as "on-channel" detection). Thus, in a common capillary tube arrangement, any excitation light required to excite the sample and any emission light coming from the sample must be transmitted through the wall of the capillary tube. A drawback of this approach is that the fused silica capillary tubes often used in CE have numerous surfaces to reflect or scatter light. Problems associated with light scattering are particularly problematic when it is desired to detect fluorescence from samples located in a plurality of closely-spaced capillary tubes by fluorescence because the scattered emmission light from one capillary tube can interfere with the detection of samples in neighboring capillary tubes.

One approach to solving the problem of on-channel detection has been to detect a sample after the sample emerges from the capillary (referred to as "off-channel" detection). In one type of arrangement, such off-channel detection takes place in a detection cell positioned downstream of the capillary tube outlets. Typically, the detection cell is configured to exhibit superior optical characteristics, e.g., a flat quartz chamber. In one class of these systems, a "sheath flow" of liquid is used to transport the sample from the outlet of the CE capillary tube to a detection zone at which detection of the sample takes place (Takahashi; Dovichi). A drawback of sheath flow systems is that, in order to avoid distortion of a sample zone in the detection cell, precise control of the flow rate of the sheath flow liquid is required. A second drawback of sheath flow systems is that the pressure used to drive the flow of the sheath flow liquid can cause back flow of the separation medium in the separation capillary tube, thereby negatively impacting resolution.

In another class of off-channel detection systems, a sample zone is transported from the outlet of a CE capillary tube to a detection zone located in a detection cell by electrophoresis under the influence of the same voltage difference used to conduct the electrophoretic separation (Takahashi). However, because of the larger cross-sectional area within the detection cell as compared to the lumen of the capillary tube, the electric field diverges at the capillary tube outlet causing a distortion of the sample zone as it enters and traverses the detection zone. Unchecked, such distortion can result in a severe loss of spatial resolution between adjacent sample zones exiting a single capillary tube and/or between sample zones exiting adjacent capillary tubes. This loss of spatial resolution tends to reduce the detectability of neighboring sample zones.

SUMMARY OF THE INVENTION

Generally, the present invention relates to a device and method for electrophoretically transporting a sample zone from an electrophoresis channel, via an outlet end thereof, into a detection zone or chamber downstream of the channel, where the distortion of the sample zone is controlled in a fashion permitting enhanced detectability.

The various embodiments of the device and method of the present invention find particular application in automated polynucleotide sequencing systems employing fluorescence detection and a plurality of separation channels (e.g., capillary electrophoresis tubes or microfabricated (e.g., etched) channels in a plate).

More particularly, in one of its aspects, the present invention relates to an analyte separation device, such as a CE tube or plate device, including (i) a plurality of separation channels, with each channel comprising an inlet end and an outlet end; (ii) a detection zone proximate the outlet ends; and (iii) at least one excitation-beam pathway extending through at least a portion of said detection zone. In an embodiment of the device, two or more of the channels have a variation region, in which the channel cross-sectional area varies (e.g., progressively increases), in the vicinity of (i.e., near and/or along) their outlet ends.

The device can further include an excitation-beam source for directing an excitation beam along said excitation-beam pathway(s). Any suitable beam source can be employed. In an embodiment of the invention, the beam source is a laser. The present invention contemplates for example (without limitation): a side-entry beam arrangement, a scanning or fanned beam (or other broad) illumination arrangement, and/or an up-channel (axial) illumination arrangement. In an embodiment of the latter, sample excitation takes place at, or not far beyond, the variation region of each channel.

In another of its aspects, the present invention relates to an analyte separation device, such as a CE tube or plate device, having an off-channel detection arrangement. In one embodiment, the device includes (i) a plurality of separation channels, each channel comprising an inlet end and an outlet end; (ii) a detection chamber, or zone, proximate the outlet ends; and (iii) an excitation-beam pathway extending through at least a portion of the detection chamber, with the pathway (a) being located on a side of the outlet ends opposite the inlet ends (i.e., downstream of the outlet ends) and (b) extending along a plane defined by the channels (e.g., a side-entry arrangement). Two or more of the channels are provided with a variation region, in which the channel cross-sectional area varies, along a region near respective outlet ends.

According to one embodiment, the cross-sectional area of the variation region increases along a direction extending from the inlet end to the outlet end. In another embodiment, the cross-sectional area of the variation region decreases along a direction extending from the inlet end to the outlet end. In a further embodiment, the variation region comprises a first portion in which the cross-sectional area decreases along a direction extending from the inlet end to the outlet end, and a second portion in which the cross-sectional area increases along said direction, with the second portion being immediately proximate and extending to the outlet end.

The variation region of at least two of the channels is preferably located in the vicinity of the outlet end. In one embodiment, the variation region is formed within a portion of the channel extending from the channel's outlet end towards its inlet end, along no more than 40% of the channel length. That is, the variation region is disposed in a downstream region of the channel, no more than 40% of the channel length away from the channel's outlet end. For example, in a 100 mm channel, the variation region would be located along the 40 mm closest to the outlet end. In other embodiments, the variation region is formed within a portion of the channel extending from the channel's outlet end towards its inlet end along no more than 30%, 20%, 15%, 10%, 5%, and/or 3% of the channel length. That is, in these embodiments, the variation region is disposed in a downstream region of the channel, no more than 30%, 20%, 15%, 10%, 5%, and/or 3%, respectively, of the channel length away from the channel's outlet end.

One embodiment further provides a detector disposed to detect fluorescence emitted from an observation region, within the detection chamber, whereat the excitation-beam pathway intersects an imaginary axial extension of one of the channels. In a related embodiment, the detector is configured to simultaneously detect fluorescence emitted from a plurality of such observation regions, with the observation regions being spaced apart from one another. A further embodiment includes a plurality of crosstalk zones, with each crosstalk zone being located approximately midway between a respective pair of adjacent observation regions; wherein the detector is configured to disregard (i.e., not to detect) fluorescence emitted from any such crosstalk zone.

In certain embodiments of the invention, the only structure permitting fluid communication with an upstream region of the detection chamber are separation channel discharge ends. In these embodiments, no substances are required to pass along the direction of sample migration into an upstream region of said detection zone other than substances passing therein via said channel discharge ends. Thus, in these embodiments, no sheath flow liquid need be utilized.

Another aspect of the present invention relates to an analyte separation device, comprising (i) a plurality of separation channels, with each channel comprising an inlet end and an outlet end; (ii) a detection chamber proximate the outlet ends; (iii) an excitation-beam pathway extending through at least a portion of the detection chamber, with the pathway being located on a side of the outlet ends opposite the inlet ends and extending along a plane defined by the channels; and (iv) barrier structure interposed between adjacent pairs of the channels and defining, at least in part, sidewalls bounding at least a portion of such channels; with the barrier structure having an end region in the vicinity of the terminal outlets that is tapered.

According to one embodiment, the tapered region progressively narrows toward the terminal end of the barrier structure. The terminal end of the barrier structure can, for example, form a point (e.g., it can have a substantially V-shaped cross section, taken along a plane defined by the channels). According to another embodiment, the terminal end of the barrier structure is blunt. The terminal end of the barrier structure can, for example, have a U-shaped cross-section (taken along a plane defined by the channels).

In one embodiment, the tapered region includes a first portion that tapers gradually, along a direction from the inlet end to the outlet end, and a second portion, more sharply tapered than the first portion, which begins after the first portion and extends to a terminal end of the barrier structure.

In another embodiment, the tapered region includes a first portion that gradually expands, along a direction from the inlet end to the outlet end, and a second portion, which begins after the first portion, that narrows to a terminal end of the barrier structure.

One embodiment further includes a detector disposed to detect fluorescence emitted from an observation region, within the detection chamber, whereat the excitation-beam pathway intersects an axial extension of one of the channels. In a related embodiment, the detector is configured to simultaneously detect fluorescence emitted from a plurality of such observation regions, with the observation regions being spaced apart from one another. Another embodiment further includes a plurality of crosstalk zones, with each crosstalk zone being located midway between a respective pair of immediately adjacent observation regions; wherein the detector is configured to disregard fluorescence emitted from any such crosstalk zone.

In another of its aspects, the present invention relates to an analyte separation device, comprising (i) a plurality of separation channels, each channel comprising an inlet end and an outlet end; (ii) a detection chamber proximate the outlet ends; (iii) an excitation-beam pathway extending through at least a portion of the detection chamber, with the pathway being located on a side of the outlet ends opposite the inlet ends and extending along a plane defined by the channels. The detection chamber, according to one embodiment, has a cross-sectional area, taken along a plane normal to the plane defined by the channels, within a range of from 50% to 400% of the sum of the cross-sectional areas of all of the channels, wherein the channel cross-sectional area employed in calculating such sum is the cross-sectional area predominating or prevailing along most of the channel length.

In certain embodiments, the detection chamber cross-sectional area is within a range of from 65% to 300%, a range of from 70% to 250%, a range of from 75% to 200%, a range of from 80% to 150%, a range of from 90% to 110%, a range of from 95% to 105%, and/or a range of from 98% to 102% of the sum of the cross-sectional areas of all of the channels. In one embodiment, the detection chamber cross-sectional area is equal to the sum of the cross-sectional areas of all of the channels.

One embodiment further includes a detector disposed to detect fluorescence emitted from an observation region, within the detection chamber, whereat the excitation-beam pathway intersects an axial extension of one of the channels. In a related embodiment, the detector is configured to simultaneously detect fluorescence emitted from a plurality of such observation regions, with the observation regions being spaced apart from one another. A further embodiment includes a plurality of crosstalk zones, with each crosstalk zone being located midway between a respective pair of immediately adjacent observation regions; wherein the detector is configured to disregard fluorescence emitted from any such crosstalk zone.

Still a further aspect of the present invention relates to an analyte separation device, comprising (i) a plurality of separation channels, each channel comprising an inlet end and an outlet end; (ii) a detection chamber proximate the outlet ends; (iii) an excitation-beam pathway extending through at least a portion of the detection chamber, with the pathway being located on a side of the outlet ends opposite the inlet ends and extending along a plane defined by the channels. A detector is disposed to simultaneously detect fluorescence emitted from a plurality of spaced-apart observation regions within the detection chamber, with each of the observation regions being located whereat the excitation-beam pathway intersects an axial extension of a respective one of the channels. Further included are a plurality of crosstalk zones, with each crosstalk zone being located midway between a respective pair of immediately adjacent observation regions; wherein the detector is configured to disregard fluorescence emitted from any such crosstalk zone.

In one embodiment, two or more of the channels have a variation region, in which the channel cross-sectional area varies, near the outlet end.

In another embodiment, the detection chamber has a cross-sectional area, taken along a plane normal to the plane defined by said channels, within a range of from 50% to 400% of the sum of the cross-sectional areas of all of the channels.

Another aspect of the present invention provides a method for reducing distortion of a sample zone (typically taking the form of a "band") upon exiting an electrophoretic channel containing a separation medium, comprising (a) loading a sample into the channel at an inlet end thereof (e.g., a sample-loading region); (b) applying an electric field along the channel in a manner effective to cause the sample to migrate through the medium and resolve into one or more sample zones; (c) changing the cross-sectional area of each sample zone as the sample zone passes along the vicinity of an outlet end of the channel (the cross-sectional area being taken along a plane perpendicular to the direction of sample zone travel); (d) ejecting the sample zone from the channel via the outlet end; and (e) analyzing the sample zone for the presence of one or more analytes of interest.

In one embodiment, step (e) is performed after step (d).

According to one embodiment, the method is performed on a plurality of samples in parallel, employing a plurality of channels.

In one embodiment, the channels are disposed side by side (e.g., in a linear array).

In one embodiment of the method, step (e) comprises (i) directing an excitation beam along a beam pathway which is located downstream of the channels and which extends along a plane defined by the channels; and, (ii) simultaneously detecting for fluorescence emitted from a plurality of spaced-apart observation regions, each of the observation regions being located whereat the excitation-beam pathway intersects an axial extension of a respective one of the channels. In a related embodiment, step (e) further comprises (iii) disregarding (ignoring) fluorescence emitted from any one or more of a plurality of crosstalk zones, wherein each crosstalk zone is located midway between a respective pair of immediately adjacent observation regions.

Still a further aspect of the present invention relates to a method for reducing distortion of sample zones (e.g., bands) upon exiting electrophoretic channels containing a separation medium, comprising (a) loading a plurality of separation channels with respective samples; (b) applying an electric field along the channels in a manner effective to cause the samples to migrate through the medium and resolve into one or more sample zones; (c) transferring each sample zone from its respective channel into a detection zone or chamber having a cross-sectional area, taken along a plane perpendicular to the direction of sample zone travel, within a range of from 50% to 400% of the sum of the cross-sectional areas of all of the channels.

One embodiment of the method further comprises (d) directing an excitation beam along a beam pathway that traverses at least a portion of the detection chamber, downstream of the channels, and extends along a plane defined by the channels; and (e) simultaneously detecting for fluorescence emitted from a plurality of spaced-apart observation regions, each of the observation regions being located whereat the excitation-beam pathway intersects an axial extension of a respective one of the channels.

A further embodiment of the method further comprises, while performing (e), (f) disregarding fluorescence emitted from any one or more of a plurality of crosstalk zones, wherein each crosstalk zone is located midway between a respective pair of immediately adjacent observation regions.

In another of its aspects, the present invention relates to a method for analyzing a plurality of sample zones (e.g., bands) upon exiting electrophoretic channels containing a separation medium, comprising: (a) directing an excitation beam along a beam pathway which is downstream of the channels and which extends along a plane defined by the channels; (b) simultaneously detecting for fluorescence emitted from a plurality of spaced-apart observation regions, each of the observation regions being located whereat the excitation-beam pathway intersects an axial extension of a respective one of the channels; and (c) disregarding fluorescence emitted from any one or more of a plurality of crosstalk zones, wherein each crosstalk zone is located midway between a respective pair of immediately adjacent observation regions.

In one embodiment of the method, (b) and (c) are carried out simultaneously.

A further aspect of the present invention relates to an analyte separation device, comprising (i) an array of elongate channels through which one or more samples are intended to migrate under the influence of a motive force (e.g., voltage) along the channels, with each channel including a sample-loading region and a terminal outlet downstream of the sample-loading region; (ii) a detection chamber downstream of the channel outlets, with each of the outlets communicating a respective channel with the detection chamber; and wherein each of the channels defines in part a sample-migration pathway extending longitudinally along such channel, passing through a respective outlet and traversing at least a portion of the detection chamber; and (iii) an unobstructed, excitation-beam pathway extending through the detection chamber, along which an excitation beam of light may be directed so as to simultaneously intersect, in the detection chamber, plural sample-migration pathways.

Two or more of the channels can be provided with a flow cross-sectional area (i.e., a cross-sectional area cutting through the channel along a plane normal to the direction of sample migration) that varies along a region near the terminal outlet. In one embodiment, the flow cross-sectional area increases along the direction of sample migration in the varying region. In another embodiment, the flow cross-sectional area decreases along the direction of sample migration in the varying region. In a further embodiment, in the varying region, the flow cross-sectional area includes a portion that decreases along the direction of sample migration, and a portion that increases along the same direction, the latter being proximate and extending to the terminal outlet.

In one embodiment, the detection chamber accommodates an electrode (e.g., an anode) toward which the sample zones migrate.

Another aspect of the present invention relates to an analyte separation device, comprising (i) an array of elongate channels through which one or more samples are intended to migrate under the influence of a motive force across the channels, with each channel including a sample-loading region and a terminal outlet downstream of the sample-loading region; (ii) a detection chamber downstream of the channel outlets, with each of the outlets communicating a respective channel with the detection chamber; wherein each of the channels defines in part a sample-migration pathway extending longitudinally along such channel, passing through a respective outlet and traversing at least a portion of the detection chamber; (iii) an unobstructed, excitation-beam pathway extending through the detection chamber, along which an excitation beam of light may be directed so as to simultaneously intersect, in the detection chamber, plural sample-migration pathways; and barrier structure interposed between adjacent pairs of the channels and defining, at least in part, sidewalls of such channels; with the barrier structure having an elongate terminal end region near the terminal outlets that is tapered.

In one embodiment, the tapered region progressively narrows to the terminal end of the barrier structure.

In another embodiment, the tapered region includes a first portion that tapers gradually along the direction of sample migration, and a second portion, more sharply tapered than the first portion, which begins after the first portion and extends to a terminal end of the barrier structure.

Still a further aspect of the present invention relates to an analyte separation device, comprising (i) an array of elongate channels through which one or more samples are intended to migrate under the influence of a motive force across the channels; each channel including a sample-loading region and a terminal outlet downstream of the sample-loading region, and having a substantially uniform flow cross-sectional area along its length; (ii) a detection chamber downstream of the outlets of the channels, with each of the outlets communicating a respective channel with the detection chamber; wherein each of the channels defines in part a sample-migration pathway extending longitudinally along such channel, passing through a respective outlet and traversing at least a portion of the detection chamber; and (iii) an unobstructed, excitation-beam pathway extending through the detection chamber, along which an excitation beam of light may be directed so as to simultaneously intersect, in the detection chamber, plural sample-migration pathways. The detection chamber, in one embodiment, has a cross-sectional area (taken along a plane normal to the direction of sample migration) within a range of from 50% to 250% of the sum of the flow cross-sectional areas of all of the channels.

In one embodiment, the detection zone cross-sectional area is approximately equal to the sum of all of the separation-zone cross-sectional areas.

In another of its aspects, the present invention provides an analyte separation device including a plurality of separation channels and a post-channel detection chamber; the device comprising: (a) means for causing samples loaded at an inlet end of the device to migrate through a medium held in the channels, to thereby resolve the samples into one or more sample zones; (b) means for changing the cross-sectional area of each sample zone as the sample zone passes along the vicinity of an outlet end of a respective one of the channels (the cross-sectional area being taken along a plane perpendicular to the direction of sample zone migration); and (c) means for interrogating sample zones in the detection chamber for the presence of one or more analytes of interest.

These and other objects, features, and advantages of the present invention will become better understood with reference to the following description, drawings, and appended claims.

BRIEF DESCRIPTION OF THE DRAWINGS

The structure and manner of operation of the invention, together with the further objects and advantages thereof, may best be understood by reference to the following description taken in conjunction with the accompanying drawings, in which identical reference numerals identify similar elements, and in which.

DETAILED DESCRIPTION OF THE INVENTION

Figure 1:
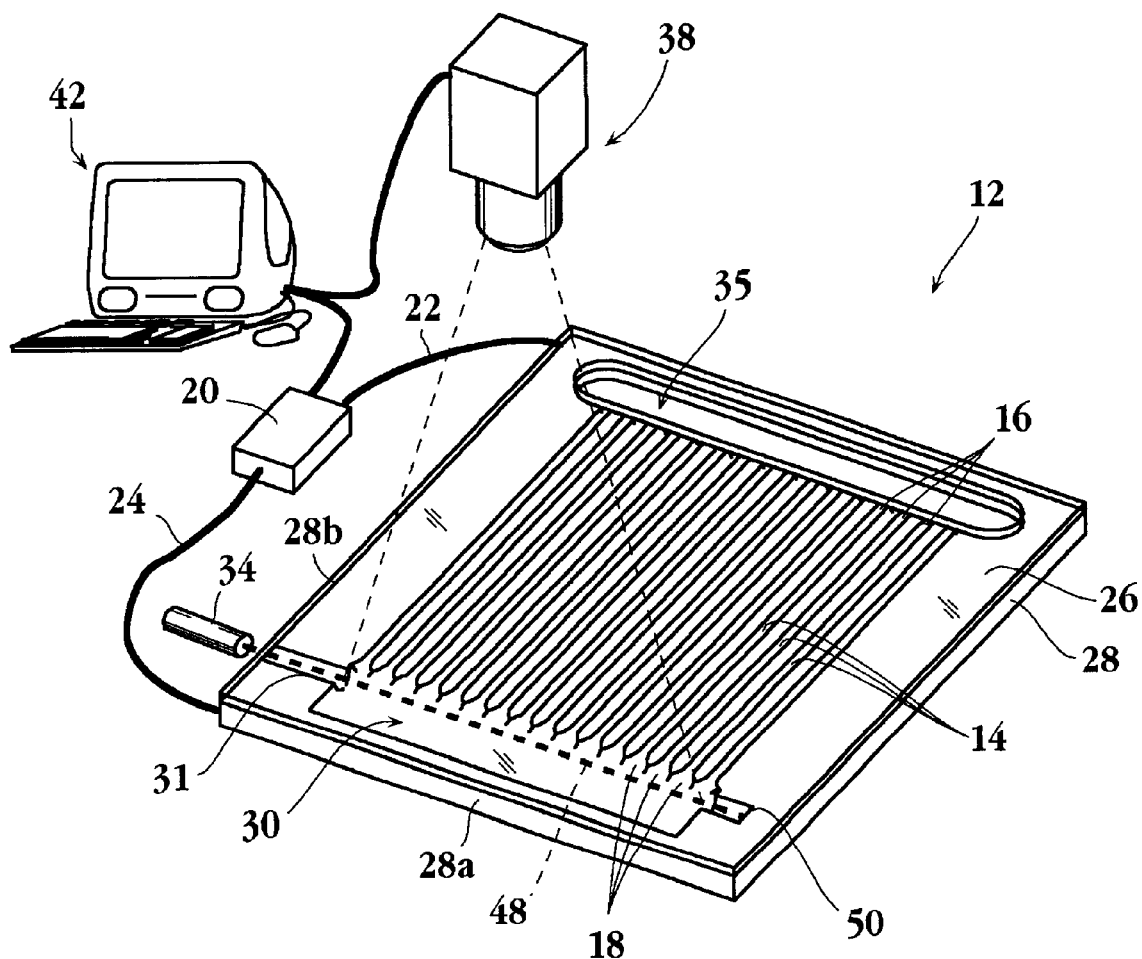
FIG. 1 is a perspective view from above of an electrophoresis system, showing an analyte separation device including a plurality of separation channels, a detection chamber, an excitation beam source, an optical detection system, and a programmed computer control/analysis system, according to an embodiment of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Unless stated otherwise, the following terms and phrases as used herein are intended to have the following meanings:

The term "channel" as used herein refers to an elongate, narrow passage or other structure (e.g., tubes, grooves, etc.) capable of supporting a volume of separation medium for carrying out electrophoresis. The geometry of a channel may vary widely. For example, a channel can have a circular, oval, semi-circular, semi-oval, triangular, rectangular, square, or other cross-section, or a combination thereof. Channels can be fabricated by a wide range of technologies, including microfabrication techniques.

The term "capillary," as used herein, has the same meaning as "channel." Exemplary "capillary" structures include, for example, a lumen of an elongated tube, or a groove formed in a chip, wafer or plate.

As used herein, the term "separation medium" refers to a medium in which an electrophoretic separation of sample components takes place. Separation media typically comprise several components, at least one of which is a charge-carrying component, or electrolyte. The charge-carrying component is usually part of a buffer system for maintaining the separation medium at a defined pH. Media for separating polynucleotides, proteins, or other biomolecules having different sizes but identical charge-frictional drag ratios in free solution, further include a sieving component. Such sieving component is typically composed of a cross-linked polymer gel, e.g., cross-linked polyacrylamide or agarose (Sambrook), or a polymer solution, e.g., a solution of polyacrylamide, hydroxyethyl cellulose, and the like (Grossman; Madabhushi).

As used herein, the term "sample zone" refers to a collection of molecules comprising a subset of sample components having similar electrophoretic migration velocities such that the molecules of a sample zone migrate as a defined zone. In the limit, a sample zone is made up of molecules having identical electrophoretic migration velocities. Sample zones are often referred to in the art as "bands."

As used herein, the term "zone distortion" refers to a change in the size, shape, and/or velocity of a sample zone; e.g., upon moving through or along a separation channel that has any variation in cross-sectional area or deviation from a straight line of migration, or upon moving from a separation channel into a detection chamber having a larger cross sectional area. Such distortion includes compression and/or expansion of the zone in the direction of migration, and/or compression and/or expansion of the zone in a direction normal to the direction of electrophoretic migration.

Generally, the present invention relates to a device and method that can provide control over the distortion of a sample zone upon exiting an electrophoresis separation channel.

Referring in detail to the drawings, FIG. 1 is a perspective view of one embodiment of an electrophoresis device, indicated generally by the reference numeral 12, constructed in accordance with the present invention. Device 12 includes a plurality of separation channels, such as elongate channels 14, with each channel having an inlet end and an outlet end, as indicated at 16 and 18 respectively. A first lead wire 22 connects a power source 20 with a first electrode (not visible in FIG. 1) disposed in electrical communication with the inlet ends of the separation channels; and a second lead wire 24 connects source 20 with a second electrode (not visible in FIG. 1) disposed in electrical communication with the outlet ends of the separation channels. In operation, a voltage is applied between the first and second electrodes, and thereby along the channels, such that a sample zone is transported from the inlet ends, to the outlet ends of the channels, and into a detection chamber, denoted as 30, located downstream of and in fluid communication with the outlet ends. According to the teachings herein (i) the downstream regions of the channels, in the vicinity of the outlet ends, and/or (ii) the detection chamber is/are configured so that distortion of one or more sample zones passing from the channels into the detection chamber can be controlled (e.g., reduced) in a fashion affording enhanced detectability.

The separation channels of the device of the invention can be any of those as defined above, or equivalents. In one preferred embodiment, the separation channels are formed on a glass or plastic substrate, such as a plate, wafer or chip, by microfabrication techniques known in the art, e.g., photolithographical and/or wet-chemical etching procedures, laser ablation, electroforming, microcontact printing, microstamping, micromolding, microcasting, micromachining, engraving, and/or embossing techniques, to name a few. Woolley et al (incorporated herein by reference) discuss certain fabrication techniques which the skilled artisan can employ in making the devices of the present invention. In another embodiment, the separation channels comprise elongated capillary tubes made from an electrically insulating material, e.g., fused silica, quartz, silicate-based glass, such as borosilicate glass, phosphate glass, alumina-containing glass, and the like, or other silica-like material(s).

In the exemplary arrangement of FIG. 1, device 12 is comprised of upper and lower plates, 26 and 28 respectively, with abutted confronting faces. Lower plate 28 is provided with a plurality of non-intersecting elongate grooves, each of roughly semi-circular or semi-oval cross-section, positioned at regular intervals (e.g., at a pitch of about 250 um) and extending along its upper face (e.g., for a length of about 5 cm); which grooves in part define separation channels 14. The lower face of plate 26 is substantially planar, and, when disposed against plate 28 as shown, further defines channels 14. Particularly, in the illustrated arrangement, the grooves of plate 28 define lower (floor) and side walls, or boundaries, of each channel 14 and the lower surface of plate 26 provides an upper wall for each channel 14.

Alternatively, both the upper and lower plates can be provided with complimentary sets of grooves that can be aligned with one another so that corresponding upper and lower grooves cooperate to define a plurality of elongate channels. Or, a plurality of elongated spacer strips can be placed at regular intervals between planar, parallel, opposed surfaces of confronting plates. The spacer strips, in such an embodiment, define the distance separating the opposed plate surfaces and the region between adjacent pairs of spacers defines, at least in part, each of a plurality of separation channels. Particularly, the lateral sides of each spacer defines channel side walls and the planar confronting plate surfaces define upper and lower walls (See, e.g., U.S. Pat. No. 5,192,412, incorporated herein by reference).

Instead of providing grooves in a lower plate which are covered by a planar lower surface of an upper plate, such as shown in FIG. 1, the device of the invention can include an upper plate with grooves formed along its lower surface, which can be placed over a planar upper surface of a lower plate (that is, essentially, the reverse of what is shown in FIG. 1). Moreover, although the device of the invention is illustrated as operating with the major planar surfaces of the plates disposed in a substantially horizontal fashion, the device instead could instead be configured to operate with the plates disposed substantially vertically, or tilted at a desired angle. These and other variations and adaptations, such as discussed next below, can readily be selected and implemented by the skilled artisan.

While the channels depicted in FIG. 1 are parallel to one another, it should be appreciated that other configurations are possible. In one embodiment, the channels converge toward one end of the device (e.g., the distance separating adjacent channels (i.e., the pitch) becomes smaller along a direction towards the outlet ends). Additionally, it should be noted that the central longitudinal axes of the channels can be straight (as shown), curved, or a combination thereof. In the embodiment of FIG. 1, the flow cross-sectional area (i.e., the cross section taken perpendicular to the direction of sample migration) is substantially the same among the various channels. In particular, the channels of FIG. 1 are all of a uniform depth (measured from the lower face of the upper plate bounding the top region of the channel to the lowermost point, or floor, of the channel groove). Such uniformity can be achieved as the ordinary result of common microfabrication methods employed in constructing the device, such as etching. However, the invention additionally contemplates channels of varying depth; which can be made, for example, by use of a two stage etching process with multiple masks.

In practice, a separation medium is injected (e.g., pressure-filled or vacuum aspirated) or otherwise provided in the separation channels of the invention to effect the electrophoretic separation of the components of the sample (s). It should be noted that the present invention contemplates the use of any suitable injection techniques; e.g., without limitation, electrokinetic injections, hydrodynamic injections, cross tee injectors and double tee injectors, etc., as known and described in the art. In one preferred embodiment, the separation medium is a flowable, non-crosslinked polymer solution.

With continued reference to FIG. 1, each of outlet ends 18 communicates a respective channel 14 with detection chamber 30, which chamber is located proximate the outlet ends. In the illustrated embodiment, detection chamber 30 is defined in part by a recessed region in lower plate 28, formed for example by an etching technique, and extends from the outlet ends 14 to a region just short of an endmost portion of the plate, indicated at 28a. The depth of the recess, in the illustrated embodiment, is like that of channels 14; however, it is not necessary that such depths be the same. Similar to the channel arrangement, the lower face of upper plate 26 serves to define an upper wall or boundary for detection chamber 30. Preferably, the depth of detection chamber 30, as measured from its floor to its upper boundary, is generally uniform throughout the chamber.

An excitation-beam source, such as 34, is provided for stimulating emission from sample zones exiting or having exited channels 14 via outlet ends 18. In a preferred embodiment, the light source is a laser, e.g., an argon ion laser, a solid state laser, or the like; however, any suitable beam source can be used. As described in more detail below, in an embodiment of the present invention, an excitation-beam pathway extends through detection chamber 30, along which an energy beam 48 generated by the beam source can pass. Such pathway is located downstream of the outlet ends and extends along a plane defined by the channels (i.e., the pathway is co-planar with the plane of the channels). In one preferred embodiment, the beam pathway is perpendicular to the direction of sample migration across the detection chamber, but this is not critical to the invention (i.e., the pathway can approach at an angle with respect to the direction of sample migration). What is important in this embodiment is that a beam passing along the pathway is capable of simultaneously exciting plural sample zones exiting or having exited different channels.

It is to be appreciated that the present invention contemplates other beam source arrangements, as well. For example, without limitation, any of the following can be employed: a side-entry beam arrangement, a scanning or fanned beam (or other broad) illumination arrangement, and/or an up-channel (axial) illumination arrangement. In an embodiment of the latter, sample excitation takes place at, or not far beyond, the variation region of each channel.

As previously mentioned, a first electrode (not visible in FIG. 1) is in electrical communication with inlet ends 16 of separation channels 14. During operation of device 12, the first electrode is maintained at a first voltage $V_1$ using power source 20. Electrical communication between the first electrode and the inlet ends of the separation channels can be established, for example, by providing an electrically conductive solution in a reservoir/loading region 35 of device 14 so that both the inlet ends of the channels and the first electrode are in contact with the conductive solution.

The second electrode (not visible in FIG. 1, but shown at 25 in FIG. 2) is in electrical communication with detection chamber 30 which is itself in electrical communication with outlet ends 18 of separation channels 14. During operation of device 12, the second electrode is maintained at a second voltage $V_2$, also using power supply 20. Preferably, electrical communication between the second electrode and detection chamber 30 is established by providing an electrically conductive solution in detection chamber 30 such that the second electrode and outlet ends 18 are in contact with the conductive solution.

The electrodes used in the device may be formed from any electrically conducting materials. Preferably, the electrodes are made from a chemically inert material, e.g., platinum, gold, stainless steel, or other relatively inert conductive material. In accordance with one embodiment of the present invention, platinum electrodes are fabricated on the top or bottom plate by RF sputtering and photolithography before the top plate is bonded to the etched bottom plate.

The electrically conductive solution used to establish electrical continuity throughout the system may be any fluid capable of transporting an electrical current. Preferably, the conductive solution is an ionic solution, e.g., an aqueous solution containing a dissolved salt. The ionic strength of the solution is preferably chosen to be high enough to mask ion depletion of the solution in the vicinity of the electrodes, but not so high as to cause excessive Joule heating. Such Joule heating is particularly disadvantageous in the detection chamber where thermal convection may lead to mixing of neighboring sample zones. Preferably, the conductive solution includes a buffer for stabilizing the pH of the solution. More preferably, the ionic composition of the conductive solution is the same in the separation channels, each of the electrode reservoirs, and the detection chamber.

Preferably, to facilitate optical detection of sample zones in the detection chamber 30, part or all of upper plate 26 covering detection chamber 30 is formed from a material which efficiently transmits light (i.e., an optically clear material), e.g., glass, quartz, clear plastic, and the like. In addition, to facilitate the introduction of an excitation light beam 48 into the detection chamber to excite fluorescence of sample zones therein, a groove 31 is formed fully extending between a left wall 28b of lower plate 28 and a neighboring side wall of detection chamber 30, so that an excitation beam 48 can pass into and across the detection chamber, as shown in FIG. 1. Alternatively, part or all of the left wall of the detection chamber can be formed from a material which efficiently transmits light. Preferably, in such an embodiment, the light-transmitting material does not significantly scatter light and has little intrinsic fluorescence. As shown in FIG. 1, an additional groove 50 can be provided in lower plate 28 on the other side of the detection chamber to act as a laser dump for a beam 48 passed across the chamber.

Further in the embodiment of FIG. 1, a detector 38 is provided for detecting sample zones passing from channels 14 via respective outlet ends 18 into detection chamber 30. The detector can be any type of detector for detecting emission of any type radiation, e.g., radioactivity, fluorescence, phosphorescence, chemi-luminescence, and the like. In a preferred embodiment, detector 38 is capable of detecting fluorescence from a plurality of locations independently and simultaneously, e.g., a CCD camera, an array of photomultiplier tubes, a diode array, and the like. As illustrated in FIG. 1, detector 38 can be connected to a computer 42 to store, analyze, and display data collected by the detector and/or to control the operation of the detector and other aspects of the device, as desired. For example, computer 42 can be programmed to control power source 20 and/or beam source 34.

It should be appreciated that, in embodiments where the sample zones are detected outside of the separation channels (i.e., downstream of the channels), non-optically clear materials may be used to form the channels, e.g., polymeric materials such as Teflon, silicone, and the like. Of course, the detection chamber, as previously mentioned, preferably permits light to pass to the detector. Although not critical to practicing the invention, certain embodiments herein prefer the use of upper and lower plates that are each optically clear in their entirety (e.g., a transparent glass or plastic material).

Figure 2:
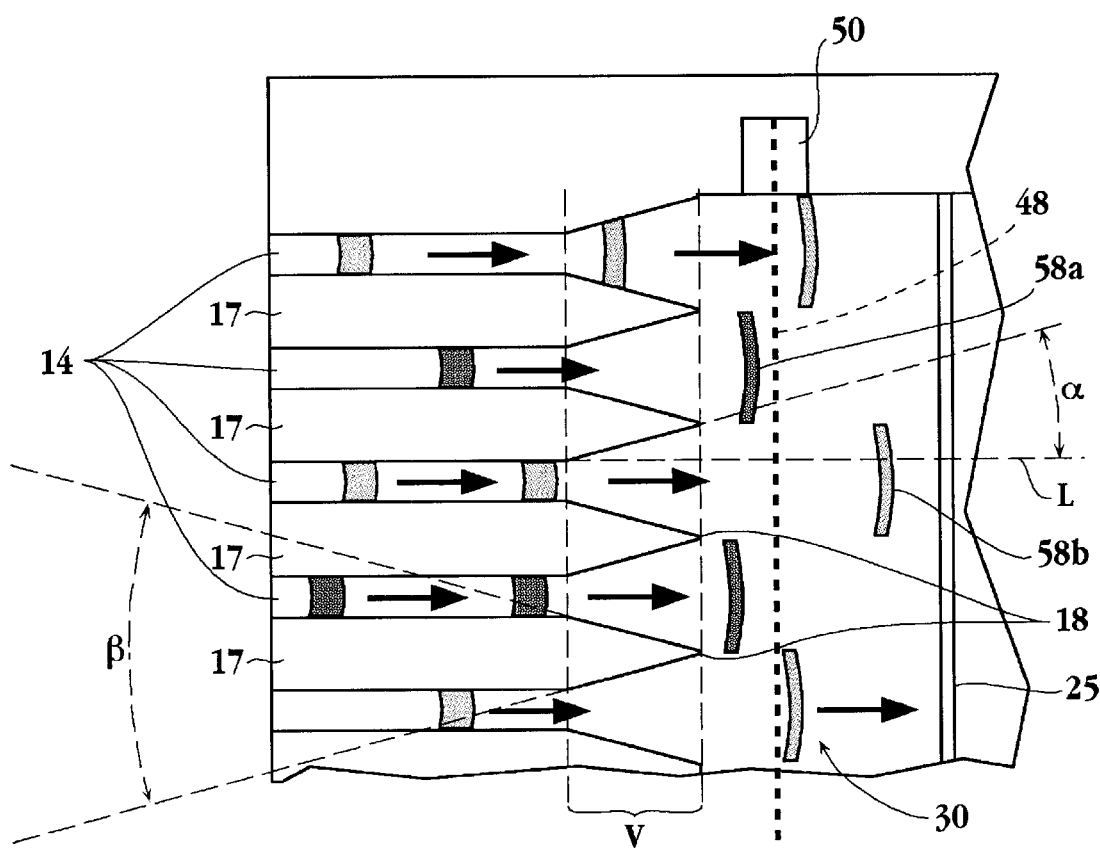
FIG. 2 is a view looking down on a downstream portion of the device of FIG. 1, showing details of the separation channels in the vicinity of their outlet ends, and details of the detection chamber including an electrode disposed therein; and further showing exemplary sample zones migrating down the device toward the electrode.

The outlet ends of the separation channels of the embodiment of FIG. 1 are shown in greater detail in FIG. 2. It can be seen that each channel 14 is provided with a variation region, V, in which the channel cross-sectional area varies, in the vicinity of a respective outlet end. The variation region provides control over the migrating sample zone as it leaves a respective channel and enters the detection chamber. In this embodiment, the variation region is configured so as to reduce the tendency of sample zones to distort (as compared to what would otherwise occur in the absence of a variation region) as they migrate from respective channels into the detection chamber. The particular geometry chosen for the variation region is not critical, provided only that sample zone distortion is reduced to some extent.

In certain preferred embodiments of the present invention, each channel is configured with a substantially uniform cross-sectional area along much of its length (that is, a selected cross-sectional area is predominant along a substantial portion of each channel), except at an end portion of the channel whereat the channel cross-sectional area progressively increases to the channel's outlet end. In the embodiment of FIG. 2, for example, along the direction of sample zone migration, the variation region begins abruptly and steadily increases such that the variation region defines an angle, with respect to a linear extension of a line, L, running longitudinally along the channel sidewall from a point upstream of the variation region. Angle can be any suitable acute angle, e.g., in one embodiment between 5 and 85 degrees, in another embodiment between 10 and 60 degrees, and in yet a further embodiment between 15 and 45 degrees. In one exemplary arrangement, angle is within a range of from 15 to 20 degrees, e.g., is 17 or 18 degrees. The increase in cross section of the variation region, in this embodiment, is achieved by increasing the channel diameter (note, also referred to as "channel width" herein, and meaning the distance from one lateral side wall to the opposing lateral side wall) of the channels in such region progressively along a direction toward the channel's terminal end. In addition or as an alternative, other embodiments contemplate increasing the upper and/or lower (floor) walls of the channel. In a multi-capillary tube embodiment of the invention, the channels expand at their ends in a fashion analogous to a funnel or a horn.

Figure 4:
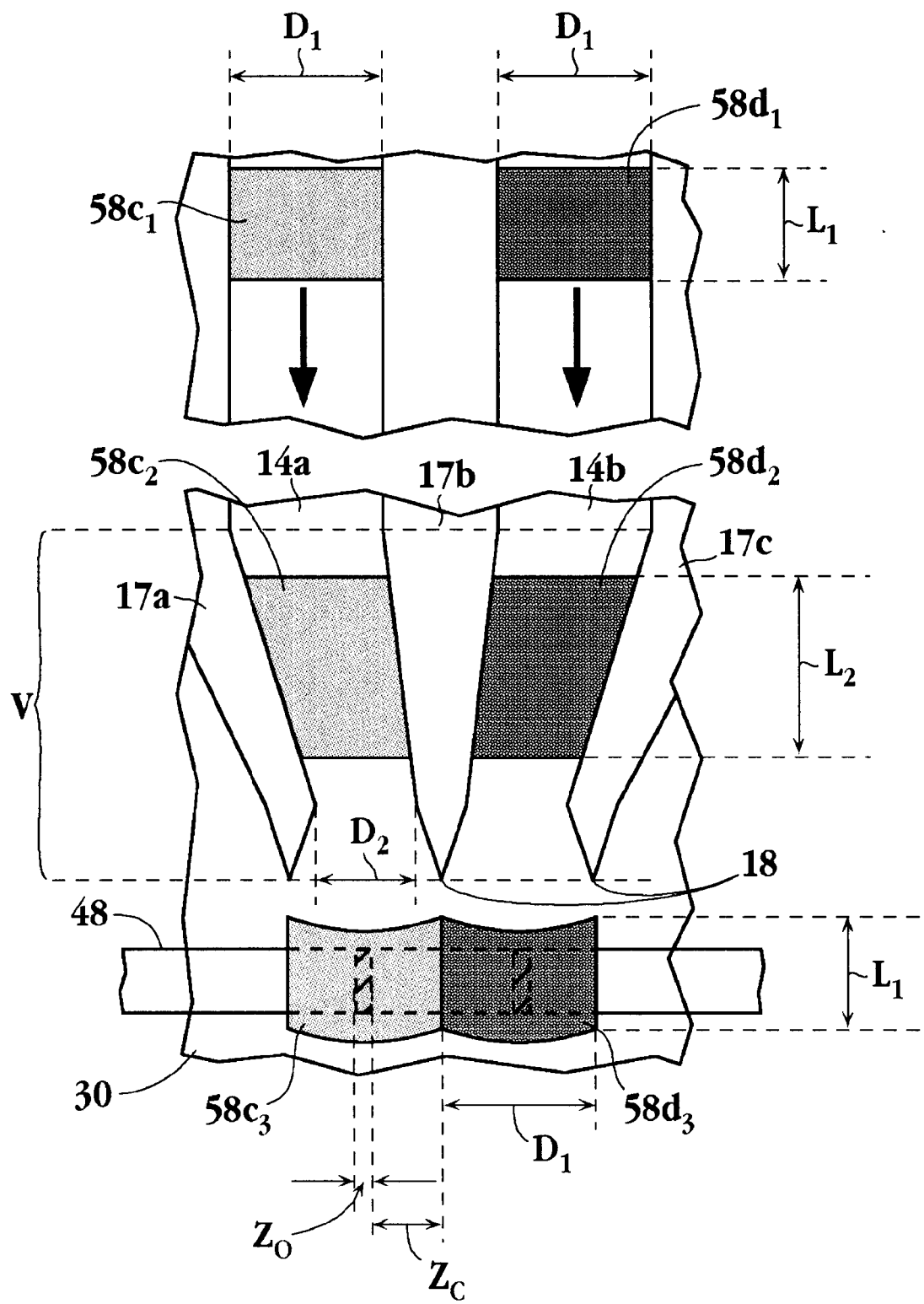
FIG. 4 is a view looking down on a downstream portion of yet another embodiment of an analyte separation device, showing details of the separation channels in the vicinity of their outlet ends, and details of a detection arrangement; and further showing exemplary sample zones migrating down the device and across the detection chamber; according to the teachings of the present invention.

At this point, it should be noted that (i) "channel width" and (ii) "sample-zone width", or "band-width", refer to "widths" measured along different directions. As mentioned above, "channel width," as used herein, means the distance from one lateral side wall of a channel to the opposing lateral side wall. "Sample-zone width" or "band width", on the other hand, is measured as the distance separating the leading (forward) face of a sample zone and the trailing (rearward) face of such zone, along the direction of sample migration. The latter definition is in accordance with the phrase of art "full width at half maximum" (FWHM), which, with reference to a plot of detected intensity vs. time or scan number, refers to a peak's width at half height. In FIG. 4, the dimensions $L_1$ and $L_2$ correspond to the FWHM of the respective sample zones. "Sample-zone length" or "band length", as used herein, is measured in the same manner as just described for sample-zone width. "Sample-zone diameter" or "band diameter", as used herein, is the distance across a sample zone along a direction normal to the direction of band migration.

It should also be noted that a variety of geometries are contemplated herein for the variation region. For example, viewed from above in cross section along a plane defined by the longitudinal axes of the channels, the variation region can be rectilinear, curved, or a combination thereof. The variation region can be, for example, V-shaped, V-shaped except with outwardly curved end portions, etc. Moreover, and as discussed further below, the variation region can itself have subsections of differing, variable cross-section (e.g., a portion of decreasing cross-sectional area and a portion of increasing cross-sectional area).

As mentioned above, the variation region of each channel is located in the vicinity of the channel's outlet end. For example, in one embodiment, the variation region is formed within a portion of the channel extending from the channel's outlet end towards its inlet end, along no more than 40% of the channel length. That is, the variation region is disposed in a downstream region of the channel, no more than 40% of the channel length away from the channel's outlet end. For example, in a 100 mm channel, the variation region according to such an embodiment would be located along the 40 mm closest to the outlet end. In other embodiments, the variation region is formed within a portion of the channel extending from the channel's outlet end towards its inlet end along no more than 30%, 20%, 15%, 10%, 5%, and/or 3% of the channel length. That is, in these embodiments, the variation region is disposed in a downstream region of the channel, no more than 30%, 20%, 15%, 10%, 5%, and/or 3%, respectively, of the channel length away from the channel's outlet end.

Such aspects of the present invention can alternatively be described in terms of barrier structure that separates adjacent pairs of channels. For example, barrier structure, denoted as 17 in FIG. 2, can define walls bounding the lateral sides of channels 14. A downstream portion of barrier structure 17 can include an end region that is tapered. In the illustrated embodiment, the barrier structure progressively narrows to a point, having essentially a V-shaped cross section, taken along a plane defined by the channels. The side walls of the barrier structure in this embodiment form an angle, that is about 20 degrees. Other embodiments contemplate an angle within a range of from about 5 to about 80 degrees, e.g., in one embodiment from about 5 to about 60 degrees, in another embodiment from about 8 to about 40 degrees, and in yet a further embodiment from about 10 to about 25 degrees; e.g., angle can be 10, 15, 20 or 25 degrees. Generally, a relatively small angle is preferred, to realize a greater distortion-lessening effect.

Figure 2A:
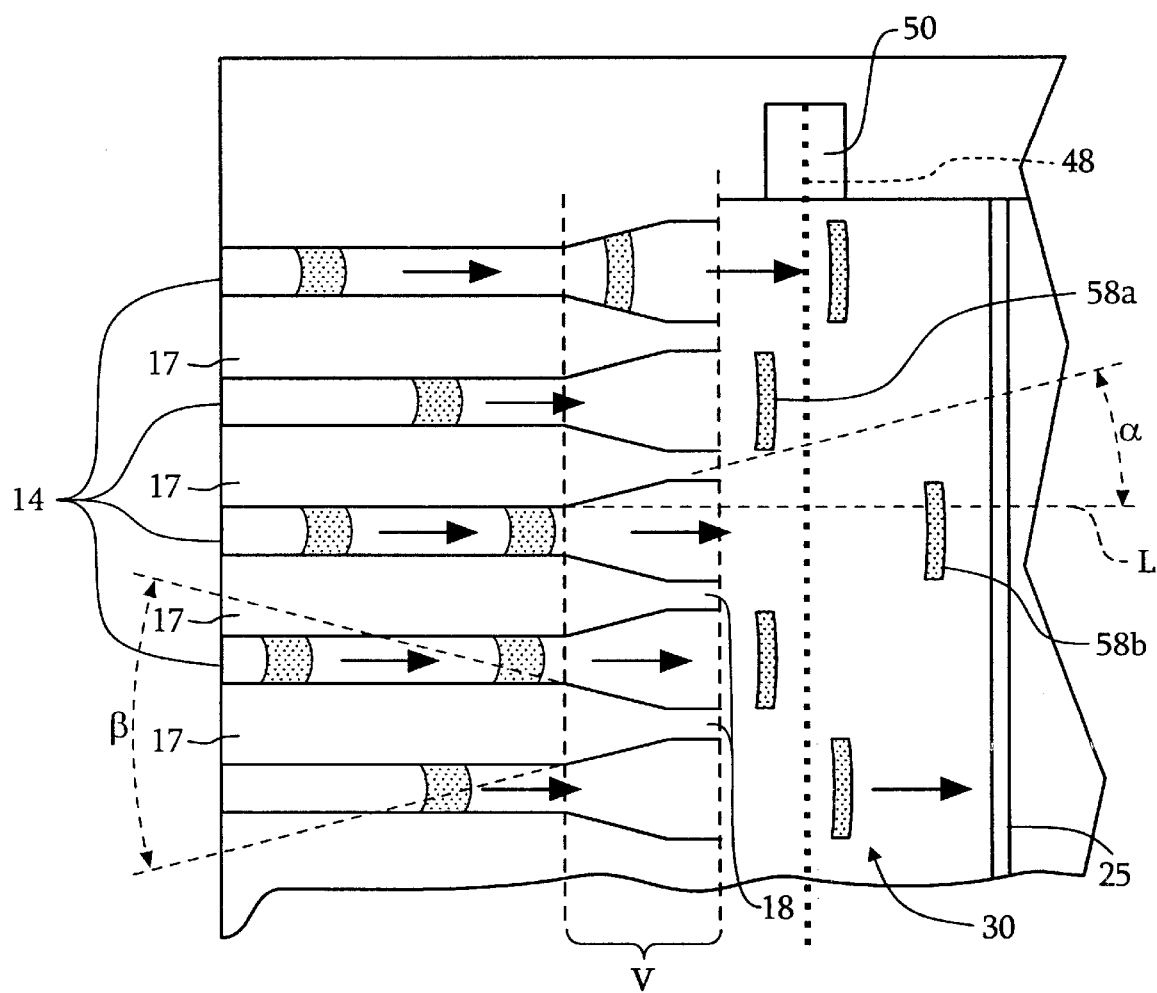
FIG. 2a is a view looking down a downstream portion of an alternative embodiment of the device of FIG. 1.

It should be appreciated that other configurations are possible for the tapered portion of the barrier structure, e.g., the end region of the barrier structure can be blunt (e.g., having a substantially U-shaped cross-section, taken along a plane defined by the channels), such as that illustrated in FIG. 2a. In one embodiment, depicted in FIG. 4, the tapered region of the barrier structure includes a first portion that tapers gradually, along a direction from the inlet ends to the outlet ends, and a second portion, more sharply tapered than the first portion, which begins after the first portion and extends to a terminal end of the barrier structure.

At this point it is noted that when a band enters a zone with a lower field, the decreased velocity will cause a proportional decrease in both the width of the band (leading face to trailing face) and the spacing between bands (interval). Nominally this does not change the resolution. However, a narrow band will have a smaller variance which is more easily degraded by other factors. Such factors are described in the literature (Capillary Electrophoresis Theory and Practice, Grossman and Colburn, eds., Academic Press (1992)). One factor of particular importance is the variance caused by finite detection volume. This can cause significant degradation, especially when the detection volume is not small in comparison to the band size. Also of note is local band distortion which can occur as the band enters the detection zone.

Returning now to the figures, and in particular with reference to FIG. 2, in operation, a voltage can be established across the channels to cause a plurality of sample zones to simultaneously migrate down the channels in the direction of the darkened arrows (i.e., downstream). While the sample zones, such as $58a$ and $58b$, in FIG. 2 are shown migrating in a staggered fashion such that no two zones in the detection chamber are directly adjacent one another, this will not always be the case. For example, referring now additionally to FIG. 4, sample zones $58c_3$ and $58d_3$ can be seen migrating into and across the detection chamber side by side. This can take place in the device of FIG. 2 and other configurations contemplated herein, as well. Under such circumstances, the lateral edge regions of samples may abut as the sample expands in a direction normal to the direction of electrophoretic migration, resulting in a potentially problematic (in terms of detection) crosstalk zone, $Z_C$. Accordingly, it may be desirable to employ means to reduce or eliminate the potentially detrimental effects that cross-talk can have on analyte detection. One approach, as contemplated herein, is to image only a centrally-located region, referred to herein as an observation zone, $Z_O$, of each sample zone onto a CCD or other detector, using pixels distant from the crosstalk zone. In FIG. 4, the intersection of each observation zone $Z_O$ with the excitation beam (two of such intersections being shown as hatched regions in FIG. 4) will map, via appropriate conventional optics, to particular pixels on a CCD, or other detector, that can be binned in the detection process. It is noted that each observation zone $Z_O$ generally aligns with an imaginary axial extension (not depicted) of a respective one of the channels along a region proximate the channel's outlet end. This "cookie cutter" approach both mitigates the negative impact that crosstalk can have on detection and improves the resolution by discarding the distorted section of the sample zones near the crosstalk zones.

Attention is now directed to barrier structure $17b$ interposing channels $14a$ and $14b$ in the embodiment of FIG. 4. It is noted that structure $17b$ includes a tapered region with a first portion that tapers gradually, along a direction toward outlet end 18, and a second portion, more sharply tapered than the first portion, which begins after the first portion and extends to a terminal end of the barrier structure (i.e., to outlet end 18). Barrier structures $17a$ and $17c$ can be seen to have similar configurations. As a result, the lumen of channels $14a$, $14b$ can be seen to narrow and subsequently expand, along the direction of band migration (darkened arrows), in the vicinity of outlet end 18. Such multi-tapered structure can be advantageous in helping to generally match the dimensions of the sample zones prevalent prior to their reaching the variation region, V, with the dimensions which the sample zones assume at the time of intersecting excitation beam 48. For example, along the region of channels $14a$, $14b$ where sample zones $58c_1$ and $58d_1$ are shown, the zones have a diameter $D_1$, which is dictated by the internal diameter of each channel at such region (e.g., 300 um), and a length $L_1$ (as previously noted, which corresponds to the FWHM for each band at its respective depicted stage of migration). Downstream, in the vicinity of outlet end 18, the diameter of sample zones $58c_2$, $58d_2$ progressively narrows as the zones pass along the first tapered portions of the barrier structures, $17a$, $17b$, $17c$; ultimately shrinking to a diameter $D_2$ (e.g., 200 um), while the length of the zones elongates to $L_2$ (e.g., $1.5 \times L_1$). Further downstream, even closer to outlet end 18, the diameter of the sample zones progressively increases as the zones pass along the second tapered portions of barrier structures, $17a$, $17b$, $17c$. As the sample zones continue to migrate, they expand in diameter as they travel across detection zone 30. Once reaching the position shown for sample zones $58c_3$ and $58d_3$, the diameter of the zones returns to $D_1$ (300 um) and their length returns to $L_1$.

Figure 3:
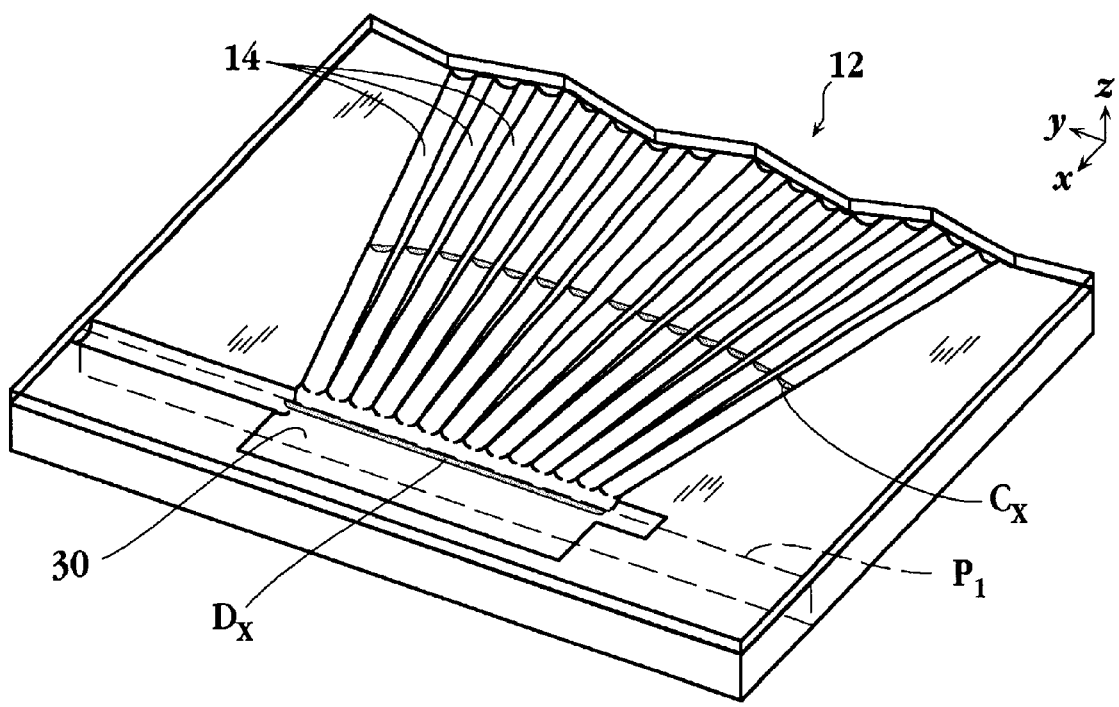
FIG. 3 is a perspective view from above of a downstream portion of another embodiment of an analyte separation device, according to the teachings of the present invention.

FIG. 3 shows a further embodiment of the present invention, also useful in providing for control over the distortion of a sample zone upon exiting an electrophoresis separation channel. Here, device 12 includes a plurality of separation channels, such as 14, which converge toward one another along a direction from their inlet ends (not shown) to detection chamber 30. In contrast to the previously-described embodiments, the channels of this embodiment do not include a variation region in the vicinity of their outlet ends (though, they can be, and are, provided with such a region in certain embodiments). Of particular importance in the illustrated embodiment, detection chamber 30 is configured with a cross-sectional area, taken along a plane, P1, normal to a plane defined by channels 14, within a range of from 50% to 400% of the sum of the cross-sectional areas of all of the channels. Preferably, the channel cross-sectional area employed in calculating such sum is the cross-sectional area predominating along most of the channel length. Thus, in embodiments having a variation region in the vicinity of the channel outlet ends (unlike that shown in FIG. 3), one would choose a sectional area upstream of such variation region; and particularly a sectional area that is the most prevalent along the length of the channel, in case the sectional area should vary elsewhere in the channel. Typically, for example, it will be useful to take a sectional area at a midpoint along each of the channels (i.e., ½ of the way down each channel's length as measured from its inlet end to its outlet end).

Sectional areas of the channels for use in the just-described summation are shown at $C_x$ in stippling in FIG. 3. The cross-sectional area along plane P1, to which the summation is compared, is shown at $D_x$ in stippling in FIG. 3.

In one embodiment, the detection chamber cross-sectional area is within a range of from 75% to 200% of the sum of the cross-sectional areas of all of the channels. In another embodiment, the detection chamber cross-sectional area is within a range of from 80% to 150% of the sum of the cross-sectional areas of all of the channels. In a further embodiment, detection chamber cross-sectional area is within a range of from 90% to 110% of the sum of the cross-sectional areas of all of the channels. In yet another embodiment, the detection chamber cross-sectional area is within a range of from 95% to 105% of the sum of the cross-sectional areas of all of the channels (e.g., they can be substantially equal).

A similar result can be achieved with the embodiment of FIGS. 1–2, for example, by decreasing the depth of detection chamber 30 (i.e., measured as the shortest distance between the floor of the recessed region in plate 28 to the lower face of upper plate 26). This geometry can be fabricated in glass, for example, by way of a two-stage etch.

The electrophoresis apparatus of the present invention can also include one or more additional elements typically used to conduct a capillary electrophoresis process, e.g., a temperature control device for controlling the temperature of the separation channels and detection chamber. Details of these and other common features of an operable capillary electrophoresis device can be found in any number of available publications, e.g., Capillary Electrophoresis Theory and Practice, Grossman and Colburn, eds., Academic Press (1992).

It should be noted that, in some instances, one of skill in the art may choose to use less than all of the channels provided by the device of the invention to conduct separations. For instance, the left- and right-endmost channels might not be loaded with samples, while the remaining channels are so loaded.

It should be appreciated that the device of the present invention does not require the use of a sheath flow liquid in order to provide enhanced detectability of samples in the detection chamber. In fact, the embodiments described above do not require or utilize a sheath flow liquid. However, it should be noted that certain embodiments of the present invention contemplate that a sheath-flow fluid can be employed in the present invention, if desired.

All publications and patent applications referred to herein are hereby incorporated by reference to the same extent as if each individual publication or patent application was specifically and individually indicated to be incorporated by reference.

Those having ordinary skill in the electrophoresis art will clearly understand that many modifications are possible in the above preferred embodiments without departing from the teachings thereof. All such modifications are intended to be encompassed within the following claims.

What is claimed is:

1. An analyte separation device, comprising:
   a plurality of separation channels, each channel comprising an inlet end and an outlet end;
   a detection chamber proximate the outlet ends; and
   an excitation-beam pathway extending through at least a portion of said detection chamber, said pathway being located on a side of the outlet ends opposite the inlet ends;
   wherein at least one of said channels has a variation region, in which the channel cross-sectional area varies;
   wherein said plurality of separation channels radially converge towards said detection chamber.

2. The device of claim 1, wherein the cross-sectional area of said variation region decreases along a direction extending from said inlet end to said outlet end.

3. An analyte separation device, comprising:
   a plurality of separation channels, each channel comprising an inlet end and an outlet end;
   a detection chamber proximate the outlet ends; and
   an excitation-beam pathway extending through at least a portion of said detection chamber, said pathway being located on a side of the outlet ends opposite the inlet ends and extending along a plane defined by said channels;
   wherein two or more of said channels have a variation region, in which the channel cross-sectional area varies, in the vicinity of said outlet end;
   wherein the cross-sectional area of said variation region increases along a direction extending from said inlet end to said outlet end.

4. The device of claim 3, further comprising an electrode disposed at least in part in said detection chamber.

5. The device of claim 3, wherein said variation region is formed within a portion of said channel extending from said outlet end towards said inlet end along no more than 40% of the channel length.

6. The device of claim 5, wherein said variation region is formed within a portion of said channel extending from said outlet end towards said inlet end along no more than 20% of the channel length.

7. The device of claim 5, wherein said variation region is formed within a portion of said channel extending from said outlet end towards said inlet end along no more than 10% of the channel length.

8. The device of claim 5, wherein said variation region is formed within a portion of said channel extending from said outlet end towards said inlet end along no more than 5% of the channel length.

9. The device of claim 3, further comprising a detector disposed to detect fluorescence emitted from an observation region, within said detection chamber, whereat said excitation-beam pathway intersects an axial extension of one of said channels.

10. The device of claim 9, wherein said detector is configured to simultaneously detect fluorescence emitted from a plurality of such observation regions, with said observation regions being spaced apart from one another.

11. An analyte separation device, comprising:
   a plurality of separation channels, each channel comprising an inlet end and an outlet end;
   a detection chamber proximate the outlet ends;

an excitation-beam pathway extending through at least a portion of said detection chamber, said pathway being located on a side of the outlet ends opposite the inlet ends and extending along a plane defined by said channels;

a detector disposed to detect fluorescence emitted from an observation region, within said detection chamber, whereat said excitation-beam pathway intersects an axial extension of one of said channels;

a plurality of crosstalk zones, each crosstalk zone being located midway between a respective pair of immediately adjacent observation regions;

wherein said detector is configured to disregard fluorescence emitted from any such crosstalk zone;

wherein two or more of said channels have a variation region, in which the channel cross-sectional area varies, in the vicinity of said outlet end wherein said detector is configured to simultaneously detect fluorescence emitted from a plurality of such observation regions, with said observation regions being spaced apart from one another.

12. An analyte separation device and detector, comprising:

a plurality of separation channels, each channel comprising an inlet end and an outlet end;

a detection chamber proximate the outlet ends;

an excitation-beam pathway extending through at least a portion of said detection chamber, said pathway being located on a side of the outlet ends opposite the inlet ends and extending along a plane defined by said channels;

a barrier structure interposed between adjacent pairs of said channels and defining, at least in part, sidewalls bounding at least a portion of such channels; said barrier structure having an end region in the vicinity of said terminal outlets that is tapered; and at least one cross talk zone wherein the detector is configured to disregard fluorescence from said cross talk zone.

13. An analyte separation device, comprising:

a plurality of separation channels, each channel comprising an inlet end and an outlet end;

a detection chamber proximate the outlet ends;

an excitation-beam pathway extending through at least a portion of said detection chamber, said pathway being located on a side of the outlet ends opposite the inlet ends and extending along a plane defined by said channels; and a barrier structure interposed between adjacent pairs of said channels and defining, at least in part, sidewalls bounding at least a portion of such channels; said barrier structure having an end region in the vicinity of said terminal outlets that is tapered;

wherein said tapered region progressively narrows toward the terminal end of said barrier structure.

14. The device of claim 13, wherein the terminal end of said barrier structure forms a point.

15. The device of claim 13, wherein the terminal end of said barrier structure is blunt.

16. The device of claim 13, further comprising an electrode disposed at least in part in said detection chamber.

17. The device of claim 13, further comprising a detector disposed to detect fluorescence emitted from an observation region, within said detection chamber, whereat said excitation-beam pathway intersects an axial extension of one of said channels.

18. The device of claim 17, wherein said detector is configured to simultaneously detect fluorescence emitted from a plurality of such observation regions, with said observation regions being spaced apart from one another.

19. An analyte separation device, comprising:

a plurality of separation channels, each channel comprising an inlet end and an outlet end;

a detection chamber proximate the outlet ends;

an excitation-beam pathway extending through at least a portion of said detection chamber, said pathway being located on a side of the outlet ends opposite the inlet ends and extending along a plane defined by said channels; and a barrier structure interposed between adjacent pairs of said channels and defining, at least in part, sidewalls bounding at least a portion of such channels; said barrier structure having an end region in the vicinity of said terminal outlets that is tapered;

wherein said tapered region includes a first portion that tapers gradually, along a direction from said inlet end to said outlet end, and a second portion, more sharply tapered than the first portion, which begins after said first portion and extends to a terminal end of said barrier structure.

20. An analyte separation device, comprising:

a plurality of separation channels, each channel comprising an inlet end and an outlet end;

a detection chamber proximate the outlet ends;

an excitation-beam pathway extending through at least a portion of said detection chamber, said pathway being located on a side of the outlet ends opposite the inlet ends and extending along a plane defined by said channels;

barrier structure interposed between adjacent pairs of said channels and defining, at least in part, sidewalls bounding at least a portion of such channels; said barrier structure having an end region in the vicinity of said terminal outlets that is tapered;

a detector disposed to detect fluorescence emitted from an observation region, within said detection chamber, whereat said excitation-beam pathway intersects an axial extension of one of said channels;

a plurality of crosstalk zones, each crosstalk zone being located midway between a respective pair of immediately adjacent observation regions;

wherein said detector is configured to simultaneously detect fluorescence emitted from a plurality of such observation regions, with said observation regions being spaced apart from one another;

wherein said detector is configured to disregard fluorescence emitted from any such crosstalk zone.

21. An analyte separation device, comprising:

a plurality of separation channels, each channel comprising an inlet end and an outlet end;

a detection chamber proximate the outlet ends; and an excitation-beam pathway extending through at least a portion of said detection chamber, said pathway being located on a side of the outlet ends opposite the inlet ends and extending along a plane defined by said channels;

wherein said plurality of separation channels converge towards said detection chamber;

wherein said detection chamber has a cross-sectional area, taken along a plane normal to said plane defined by said channels, within a range of from 50% to 400% of the sum of the cross-sectional areas of all of the channels, wherein the channel cross-sectional area employed in calculating such sum is the cross-sectional area predominating along most of the channel length.

22. The device of claim 21, wherein said detection chamber cross-sectional area is within a range of from 75% to 200% of the sum of the cross-sectional areas of all of the channels.

23. The device of claim 21, wherein said detection chamber cross-sectional area is within a range of from 80% to 150% of the sum of the cross-sectional areas of all of the channels.

24. The device of claim 21, wherein said detection chamber cross-sectional area is within a range of from 90% to 110% of the sum of the cross-sectional areas of all of the channels.

25. The device of claim 21, further comprising an electrode disposed at least in part in said detection chamber.

26. The device of claim 21, further comprising a detector disposed to detect fluorescence emitted from an observation region, within said detection chamber, whereat said excitation-beam pathway intersects an axial extension of one of said channels.

27. The device of claim 26, wherein said detector is configured to simultaneously detect fluorescence emitted from a plurality of such observation regions, with said observation regions being spaced apart from one another.

28. The device of claim 21, wherein said detection chamber cross-sectional area is within a range of from 60% to 300% of the sum of the cross-sectional areas of all of the channels.

29. An analyte separation device, comprising:
   a plurality of separation channels, each channel comprising an inlet end and an outlet end;
   a detection chamber proximate the outlet ends;
   an excitation-beam pathway extending through at least a portion of said detection chamber, said pathway being located on a side of the outlet ends opposite the inlet ends and extending along a plane defined by said channels;
   a detector disposed to detect fluorescence emitted from an observation region, within said detection chamber, whereat said excitation-beam pathway intersects an axial extension of one of said channels;
   a plurality of crosstalk zones, each crosstalk zone being located midway between a respective pair of immediately adjacent observation regions; wherein said detector is configured to disregard fluorescence emitted from any such crosstalk zone;
   wherein said detection chamber has a cross-sectional area, taken along a plane normal to said plane defined by said channels, within a range of from 50% to 400% of the sum of the cross-sectional areas of all of the channels, wherein the channel cross-sectional area employed in calculating such sum is the cross-sectional area predominating along most of the channel length;
   wherein said detector is configured to simultaneously detect fluorescence emitted from a plurality of such observation regions, with said observation regions being spaced apart from one another.

30. An analyte separation device, comprising:
   a plurality of separation channels, each channel comprising an inlet end and an outlet end;
   a detection chamber proximate the outlet ends;
   an excitation-beam pathway extending through at least a portion of said detection chamber, said pathway being located on a side of the outlet ends opposite the inlet ends and extending along a plane defined by said channels;
   a detector disposed to simultaneously detect fluorescence emitted from a plurality of spaced-apart observation regions within said detection chamber, each of said observation regions being located whereat said excitation-beam pathway intersects an axial extension of a respective one of said channels; and
   a plurality of crosstalk zones, each crosstalk zone being located midway between a respective pair of immediately adjacent observation regions; wherein said detector is configured.

31. The device of claim 30, wherein two or more of said channels have a variation region, in which the channel cross-sectional area varies, in the vicinity of said outlet end.

32. The device of claim 30, wherein said detection chamber has a cross-sectional area, taken along a plane normal to said plane defined by said channels, within a range of from 50% to 400% of the sum of the cross-sectional areas of all of the channels.

33. A method for reducing distortion of a sample zone upon exiting an electrophoretic channel containing a separation medium, comprising:
   (a) loading a sample at an inlet end of said channel;
   (b) applying an electric field along the channel thereby causing the sample to migrate through the medium and resolve into one or more sample zones;
   (c) changing the cross-sectional area of each sample zone as the zone passes along the vicinity of an outlet end of said channel, said cross-sectional area taken along a plane perpendicular to the direction of sample zone travel;
   (d) ejecting the sample zone from the channel via the outlet end; and
   (e) analyzing the sample zone for the presence of one or more analytes of interest, including:
      (i) directing an excitation beam along a beam pathway which is located downstream of said channels and which extends along a plane defined by said channels;
      (ii) simultaneously detecting for fluorescence emitted from a plurality of spaced-apart observation regions, each of said observation regions being located whereat said excitation-beam pathway intersects an axial extension of a respective one of said channels; and,
      (iii) disregarding fluorescence emitted from any one or more of a plurality of crosstalk zones, wherein each crosstalk zone is located midway between a respective pair of immediately adjacent observation regions.

34. A method for reducing distortion of sample zones upon exiting electrophoretic channels containing a separation medium, comprising:
   (a) loading a plurality of separation channels with respective samples;
   (b) applying an electric field along the channels thereby causing the samples to migrate through the medium and resolve into one or more sample zones;
   (c) transferring each sample zone from its respective channel into a detection zone having a cross-sectional area, taken along a plane perpendicular to the direction of sample zone travel, within a range of from 50% to 400% of the sum of the cross-sectional areas of all of the channels;

(d) directing an excitation beam along a beam pathway that traverses at least a portion of said detection chamber, downstream of said channels, and extends along a plane defined by said channels;

(e) simultaneously detecting for fluorescence emitted from a plurality of spaced-apart observation regions, each of said observation regions being located whereat said excitation-beam pathway intersects an axial extension of a respective one of said channels; and while performing (e), (f) disregarding fluorescence emitted from any one or more of a plurality of crosstalk zones, wherein each crosstalk zone is located midway between a respective pair of immediately adjacent observation regions.

35. A method for analyzing a plurality of sample zones upon exiting electrophoretic channels containing a separation medium, comprising:

(a) directing an excitation beam along a beam pathway which is downstream of said channels and which extends along a plane defined by said channels;

(b) simultaneously detecting for fluorescence emitted from a plurality of spaced-apart observation regions, each of said observation regions being located whereat said excitation-beam pathway intersects an axial extension of a respective one of said channels; and (c) disregarding fluorescence emitted from any one or more of a plurality of crosstalk zones, wherein each crosstalk zone is located midway between a respective pair of immediately adjacent observation regions.

36. The method of claim 35, wherein (b) and (c) are carried out at the same time.

37. An analyte separation device, comprising:

(i) an array of elongate channels through which one or more samples are intended to migrate under the influence of a motive force along the channels, with each channel including a sample-loading region and a terminal outlet downstream of the sample-loading region;

(ii) a detection chamber downstream of the channel outlets, with each of the outlets communicating a respective channel with the detection chamber; and wherein each of the channels defines in part a sample-migration pathway extending longitudinally along such channel, passing through a respective outlet and traversing at least a portion of the detection chamber; and (iii) an unobstructed, excitation-beam pathway extending through the detection chamber, along which an excitation beam of light may be directed so as to simultaneously intersect, in the detection chamber, plural sample-migration pathways;

wherein at least one of the channels has a flow cross-sectional area that varies along a region in the vicinity of a respective terminal outlet;

wherein said array converges towards said detection chamber.

38. An analyte separation device, comprising:

a plurality of separation channels, each channel comprising an inlet end and an outlet end;

a detection zone proximate the outlet ends;

at least one excitation-beam pathway extending through at least a portion of said detection zone; and a beam source for directing an excitation beam along said pathway;

wherein two or more of said channels have a variation region, in which the channel cross-sectional area varies, in the vicinity of said outlet end;

wherein said channels radially converge towards said detection zone.

* * * * *